United States Patent
DeFreitas et al.

(10) Patent No.: US 7,792,244 B2
(45) Date of Patent: *Sep. 7, 2010

(54) BREAST COMPRESSION FOR DIGITAL MAMMOGRAPHY, TOMOSYNTHESIS AND OTHER MODALITIES

(75) Inventors: Kenneth F. DeFreitas, Patterson, NY (US); Linda Hopponen, New Milford, CT (US); Ian Shaw, Yorktown Heights, NY (US); Loren Niklason, Hillsborough, NC (US); Jay Stein, Boston, MA (US); Andrew P. Smith, Lexington, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/362,275

(22) Filed: Jan. 29, 2009

(65) Prior Publication Data
US 2009/0135997 A1 May 28, 2009

Related U.S. Application Data

(63) Continuation of application No. 11/729,048, filed on Mar. 27, 2007, now Pat. No. 7,489,761.

(60) Provisional application No. 60/786,529, filed on Mar. 27, 2006.

(51) Int. Cl.
*A61B 6/04* (2006.01)
(52) U.S. Cl. ........................................... 378/37
(58) Field of Classification Search ............ 378/4, 378/20, 37, 62, 64, 208
See application file for complete search history.

(56) References Cited

U.S. PATENT DOCUMENTS

| | | | |
|---|---|---|---|
| 3,963,933 A | 6/1976 | Henkes, Jr. | |
| 4,104,528 A | 8/1978 | Strax | |
| 6,128,523 A | 10/2000 | Bechtold et al. | |
| 6,143,675 A | 11/2000 | McCollam et al. | |
| 6,345,194 B1 | 2/2002 | Nelson et al. | |
| 6,397,415 B1 | 6/2002 | Hsieh | |
| 6,465,073 B1 | 10/2002 | Morman et al. | |
| 6,577,702 B1 | 6/2003 | Lebovic et al. | |
| 6,765,984 B2 | 7/2004 | Higgins et al. | |
| 6,850,590 B2 | 2/2005 | Galkin | |
| 6,968,033 B2 | 11/2005 | Lebovic et al. | |

(Continued)

FOREIGN PATENT DOCUMENTS

DE    2335576    1/1975

(Continued)

OTHER PUBLICATIONS

Jun. 5, 2008 International Search Report and Written Opinion in International Application No. PCT/US07/22271.

*Primary Examiner*—Irakli Kiknadze
(74) *Attorney, Agent, or Firm*—Cooper & Dunham LLP

(57) ABSTRACT

A breast x-ray imaging method and system that is particularly suited for tomosynthesis imaging but also is useful for conventional mammography. A fluid containing pillow or bag is placed between the breast and a paddle that compresses the breast against a breast platform covering an imaging device, to enhance patient comfort and provide other benefits. Alternatives include a flexible sheet compressing the breast, and a compressible foam, preferably contoured to accommodate a patient's breast.

17 Claims, 16 Drawing Sheets

Air pillow side view

U.S. PATENT DOCUMENTS

| | | |
|---|---|---|
| 6,975,701 B2 | 12/2005 | Galkin |
| 7,248,668 B2 | 7/2007 | Galkin et al. |
| 7,505,555 B2 * | 3/2009 | Hermann et al. ............. 378/37 |
| 2003/0174807 A1 | 9/2003 | Lebovic |
| 2005/0036584 A1 | 2/2005 | Lebovic et al. |
| 2005/0207528 A1 | 9/2005 | Hjarn |
| 2005/0249695 A1 | 11/2005 | Tiller et al. |
| 2007/0036265 A1 | 2/2007 | Jing et al. |

FOREIGN PATENT DOCUMENTS

| | | |
|---|---|---|
| DE | 29908202 | 7/1999 |
| DE | 19901724 | 7/2000 |
| FR | 2321263 | 8/1975 |
| FR | 2702059 | 2/1993 |

* cited by examiner

Figure 1 Air pillow side view

Figure 2 Air pillow top view

Figure 3 Air Pillow used between paddle and breast

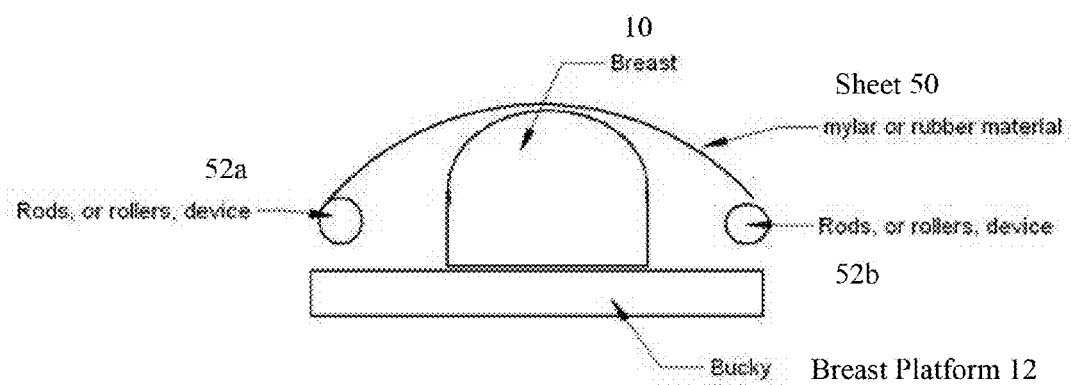
Figure 5 Compression system utilizing material stretched between two rods

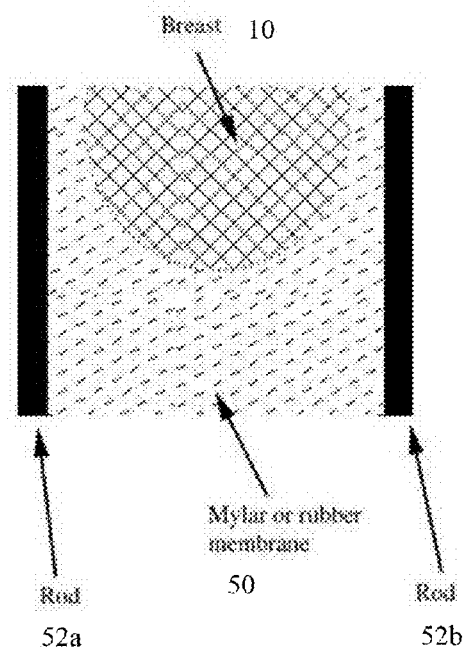
Figure 6 Top view of compression system utilizing material stretched between two rods. The breast is underneath the membrane, and is visible because the membrane is transparent.

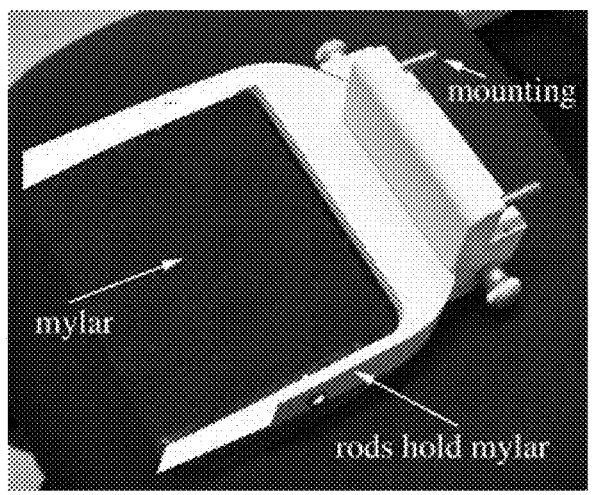
Figure 7 Compression system showing rod that mylar will be stretched across, and the mounting mechanism allowing mounting to the gantry.

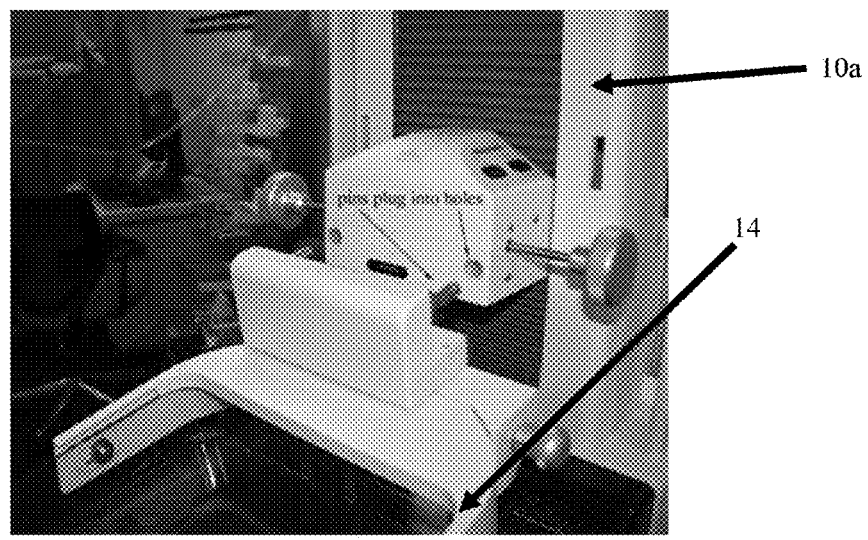
Figure 8 Shows prior art and current methods of mounting paddles to gantry

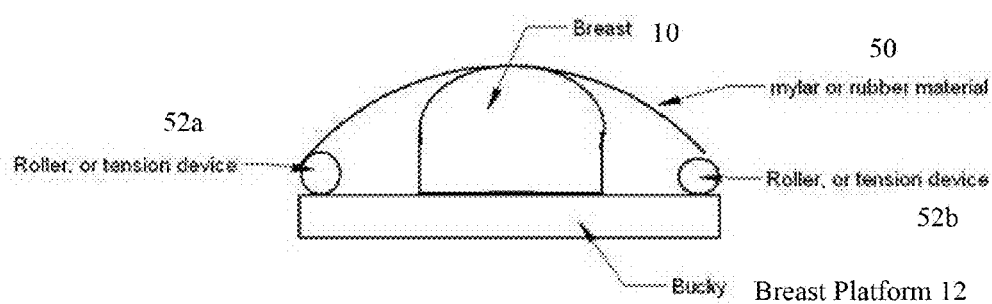
Figure 9 Compression system utilizing material stretched between two rods or rollers fastened to lower breast platform or Bucky

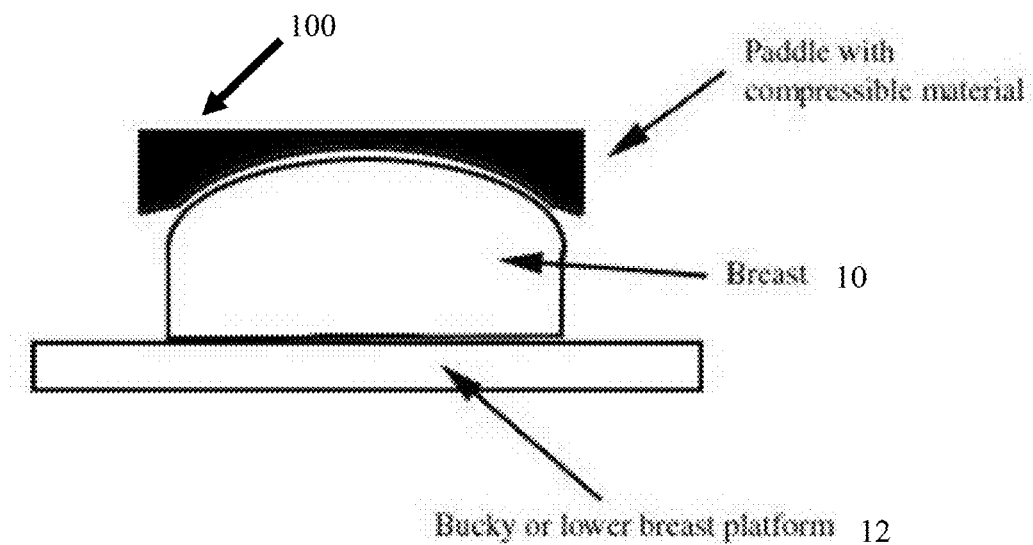
Figure10 Compression system employing a deformable compression paddle

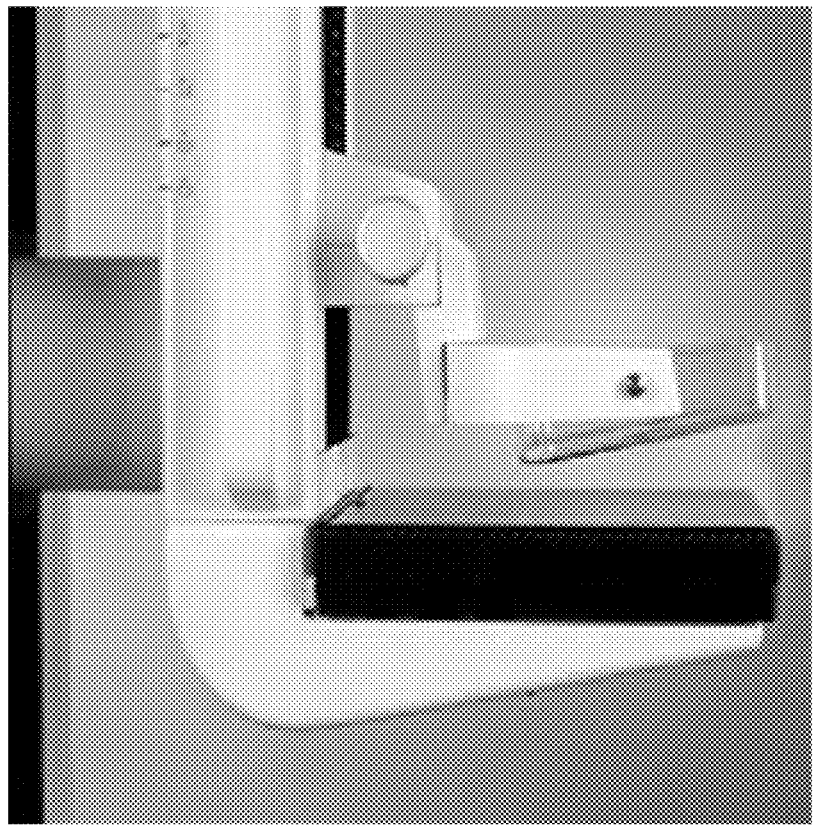
Figure 11 Prior Art.: Tilting FAST paddle by Lorad

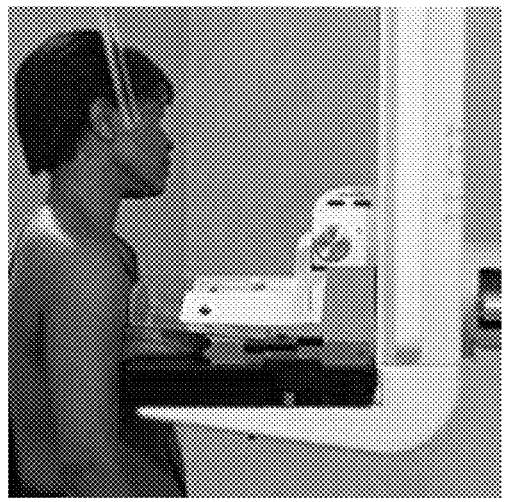
Figure 12 Prior Art: Tilting FAST paddle by Lorad showing a breast in compression

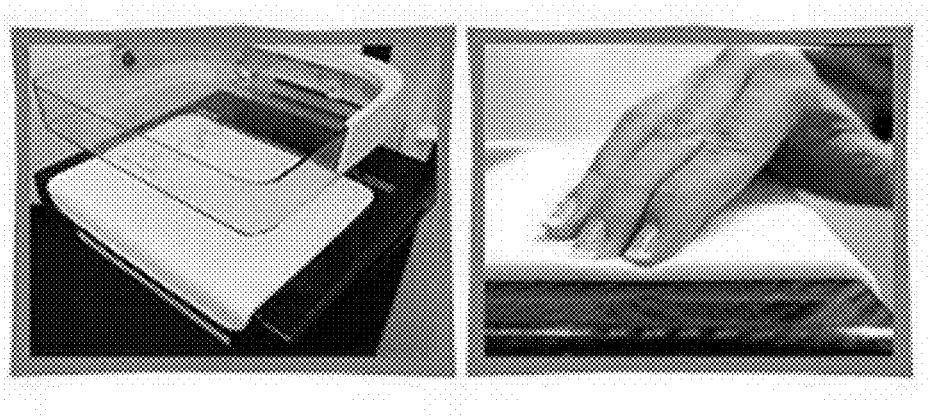
Figure 13                                    Figure 14
Prior Art: compression pads. From Biolucent website www.biolucent.com/info.html

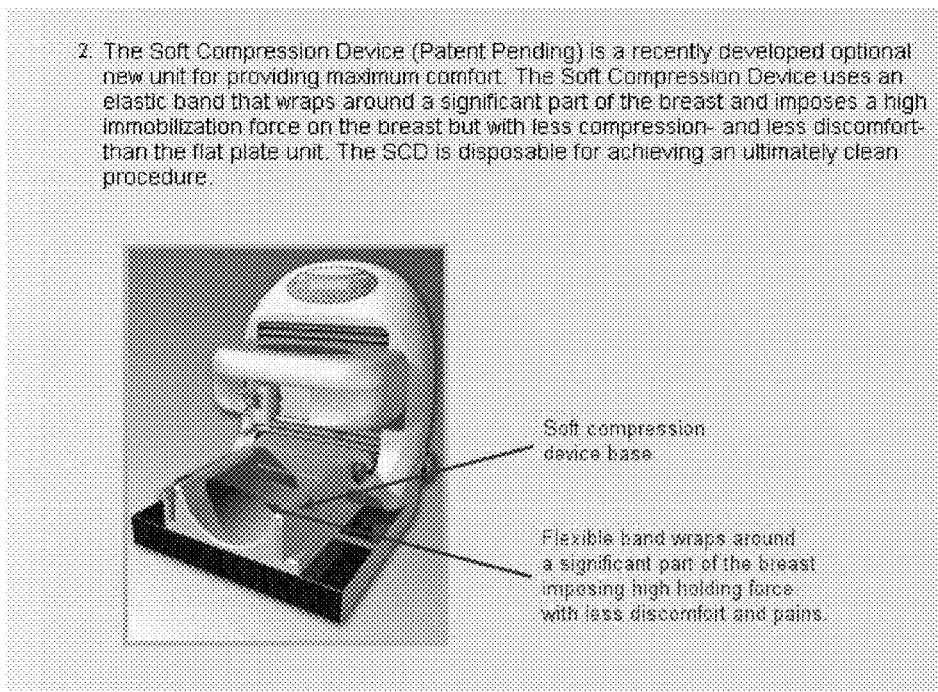
Figure 15 Prior Art. Shows compression method for biopsies. From Scientific Biopsy website: www.sbiopsy.com/Breast-Compression.htm

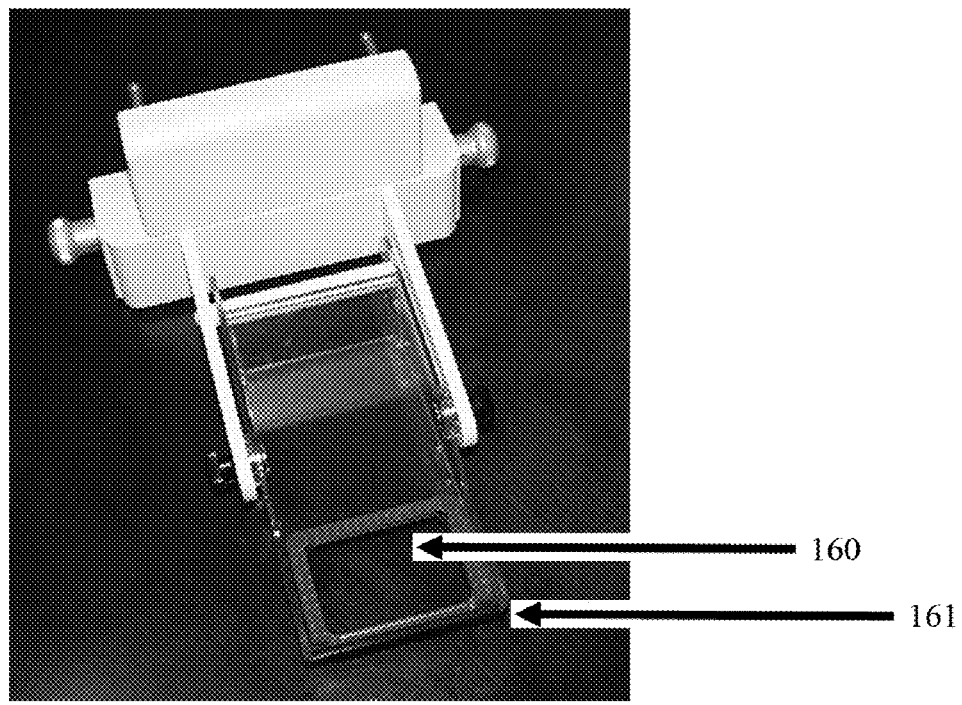
Figure 16 Paddle for needle localization or biopsy

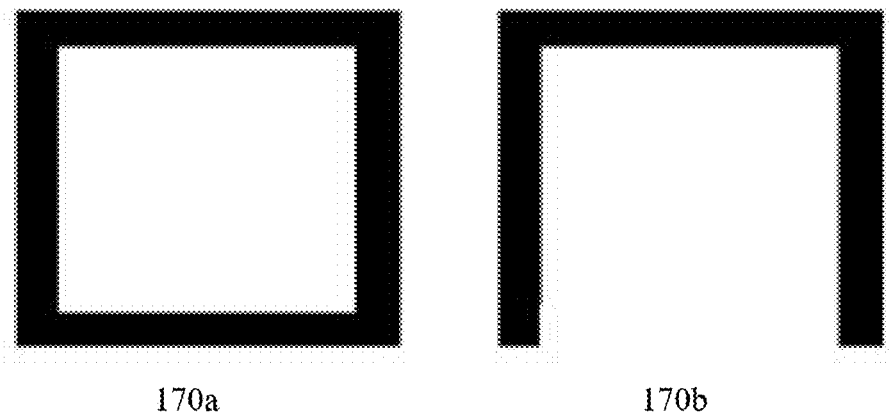
Figure 17 Shapes to accommodate cutout in paddle

US 7,792,244 B2

BREAST COMPRESSION FOR DIGITAL MAMMOGRAPHY, TOMOSYNTHESIS AND OTHER MODALITIES

CROSS-REFERENCE TO RELATED APPLICATION

This application is a Rule 1.53(b) continuation of application Ser. No. 11/729,048, filed Mar. 27, 2007 (now U.S. Pat. No. 7,489,761 ), which claims the benefit of U.S. Provisional Application Ser. No. 60/786,529, filed Mar. 27, 2006, the entire contents of which are incorporated by reference herein.

FIELD

This patent specification pertains mainly to mammography and finds particular application in digital mammography and tomosynthesis.

BACKGROUND AND SUMMARY OF THE DISCLOSURE

A significant patient concern in mammography is the discomfort the patient feels when the breast is compressed, typically between two rigid plastic surfaces, with sufficient force to spread out the breast tissues. The reasons for using such high compression include: (1) to make the breast thinner in the direction of x-ray flux and thereby reduce patient radiation exposure from the level required to image the thicker parts of an breast that is not compressed; (2) to make the breast more uniform in thickness in the direction of x-ray flux and thereby facilitate more uniform exposure at the image plane over the entire breast image; (3) to immobilize the breast during the x-ray exposure and thereby reduce image blurring; and (4) to bring breast tissues out from the chest wall into the exposure area and thus image more tissue.

Reason 2 has been relevant mainly to analog screen-film mammography imaging, which has a limited dynamic range and requires fairly specific radiation levels on the image receptor to avoid either under- or over-saturating the film. With the advent of digital mammography and its wide dynamic range, this requirement is no longer as compelling, because image processing can flatten the image post-exposure and provide a more uniform gray scale appearance even if the breast has significant thickness variations across the field of view. Breast tomosynthesis (tomo), an emerging modality that uses three-dimensional imaging, has an even lesser need for uniform breast thickness. There is therefore an opportunity to provide breast immobilization methods that are especially suited for digital mammography and tomosynthesis. Reason 1 is also less important for digital mammography and tomo, because these modalities typically can use higher average x-ray energies and keep radiation exposures low even for thicker breasts.

Standard compression methods for mammography use a movable, rigid clear plastic compression paddle. The breast is placed on a bottom breast platform that is flat, and the paddle is then compressed onto the breast, usually while the technologist is holding the breast in place and perhaps helps positioning it between the compression paddle and breast platform to ensure proper tissue coverage in the image receptor's field of view. One reason for the discomfort felt using this method is that the compression force is non-uniformly distributed throughout the breast. It is concentrated at the thickest portion of the breast, usually near the chest wall. The anterior portion of the breast, such as near the nipple, may not receive any compression force because the paddle may not even contact this portion of the breast.

Some compression paddles tilt, such as the paddle available in various sizes from Lorad of Danbury, Conn., a division of Hologic, Inc. of Bedford, Mass., under the trade name F.A.S.T. This tilting paddle provides more uniform compression across the breast, and more comfortable breast examinations. An example of such a paddle is illustrated in FIG. 11, as mounted in a mammography system commercially available from Lorad. It is illustrated in FIG. 12 as used to compress a patient's breast in a similar mammography system.

Other methods have been proposed and may have been used clinically to improve patient comfort. One is the use of relatively thin foam pads that are placed above and/or below the breast. The pad compresses during the compression procedure and may provide improved comfort by spreading out the pressure to a greater extent than using a hard-surfaced paddle and/or breast platform alone. One such pad system is proposed in U.S. Pat. Nos. 6,968,033, 6,765,984, and 6,577, 702 and published U.S. patent application US 2003/0007597 A1, all assigned on their face to Biolucent, and is believed to be on sale by Biolucent. An example thereof is illustrated in FIG. 13 and FIG. 14, when placed on the breast platform. Another pad system is proposed in U.S. Pat. Nos. 6,850,590 and 6,975,701 and published U.S. patent applications US 2006/0050844 A1, US 2004.0156472 A1 and US 2003/0099325 A1, all naming as the inventor Benjamin M. Galkin. One disadvantage of pad systems of this type is that the pads are not transparent to visible light. This means that there is impaired visibility of the breast, if the pad is used above the breast. Visibility is important for the technologist to aid in breast positioning. Another disadvantage of this solution is that the pad needs to be made of fairly dense thin form, so as to provide at least meaningful deformability under the high pressures. It is believed that this foam can creates minor artifacts in the image, especially if the pad slips during positioning and does not cover the entire breast. Another limitation is that this pad is relatively expensive to manufacture, and this makes it more expensive to use, and that it may require excessive time to secure to and then remove from the breast platform and/or compression paddle. Yet another system for improving patient comfort has been proposed for a different purpose—to immobilize the breast during biopsy—by Scientific Biopsy (www.sbiopsy.com). It is illustrated in FIG. 15 and is understood to use a soft, trough-shaped support to cradle the breast and a flexible band that wraps on top of the breast to impose a holding force. A thin plastic sheet compressing a breast for ultrasound examination rather than for x-ray imaging is proposed in published patent application US 2003/0007598 A1 (see, e.g., FIG. 7 and paragraph [0115]) but no teaching could be found that the material is transparent to visible light or that the arrangement is useful for x-ray imaging or with a flat breast platform.

The known existing methods of improving patient comfort during breast mammography are believed to have been designed with analog screen-film mammography in mind, especially the requirements of such mammography for very thin, very uniform thickness in a compressed breast. However, newer modalities such as digital mammography and tomosynthesis have different needs and constraints, offer new challenges and new opportunities, and have allowed for reconsideration the old approaches. For example, tomosynthesis methods do not need to have the patient's breast compressed to a degree that would make it substantially flat because tomosynthesis is a 3d imaging modality. In digital mammography, the breast does not need to be made as flat as for analog mammography, because image processing can effectively flatten the image. The methods proposed in the patents and applications of Biolucent identified above are understood to involve relatively thin pads designed to accomplish essentially the degree of compression and flattening of the breast that is used in analog mammography; those pads are understood to be very thin to prevent much deviation from a thin flat breast. In addition, no indication has been found in those proposals to make the pads transparent to visible light and thereby facilitate breast positioning in the compression process.

This patent specification is directed to new approaches to patient comfort that are particularly suitable for such newer modalities, and is believed to overcome a number of disadvantages of the known compression approaches.

One non-limiting example of such new approaches to patient comfort in mammography and/or tomosynthesis involves the use of a specially adapted device to control, distribute and re-direct breast compression forces. The device preferably is between the patient's breast and the compression paddle, but can be between the breast and the breast platform, or such device can be used on each side of the compressed breast. Preferably at least some of the device is transparent to visible light to facilitate positioning the breast in compression, and typically the entire device, or nearly the entire device, is made of a material transparent to visible light. In a simple example, the device can be an air-filled pillow or bag of plastic material that is transparent to visible light. Preferably, the air pressure is selected such that the bag will conform to the breast in compression in mammography or tomosynthesis such that the path of x-ray flux through air in the pillow would be short or even zero-length at the thickest part of the compressed breast and progressively longer toward the thinner parts of the compressed breast. For example, the air inside the device can be essentially at atmospheric pressure and the amount of air inside the device can be such that the walls of the device are not tight but are somewhat wrinkled. At least a portion of one or both sides of the device that contacts the breast and/or the chest wall of the patient can be made of, or covered with, a material that is sticky or otherwise has a sufficiently high coefficient of friction with the patient's skin and/or the compression surface that contacts the device, to thereby prevent or at least significantly reduce slippage during compression between the device and the patient's skin, and/or between the other side of the device and the compression surface, and to help push into the x-ray field of view and the x-ray image more of the tissue adjacent the patient's chest wall. For example, a portion of the surface that would be at or near the chest wall is made sticky. The device can be made available in different sizes and at different levels of internal air pressure. It can be stored before use with air inside, or it can be stored flat, without air or with less air inside, and pumped with air to the desired pressure when it comes time to use it. The device can be a single-use device that can be used only for a single patient, or even for a single breast or a single view, and then discarded. Alternatively, the device can be a multiple-use device that is used for more than one x-ray view and/or more than one breast of the same patient, and/or can be used for several patients. A fresh length of a thin and transparent plastic film can be placed between the patient's breast and a multiple-use device if desired. A device can be temporarily secured to the compression paddle and or the breast platform with a suitable adhesive or by use of mechanical means such as hook-and-loop strips.

The device can comprise a single compartment filled with air (or another gas) or can have two or more compartments or chambers that can, but need not, differ in internal pressure and/or in internal volume. As a non-limiting example, the device can have one compartment filled with gas a higher pressure than another, or can have more than two compartments, each filled with has at respective pressure that can be the same as, or different from, that of other compartments that can have the same or different internal volumes. For example, a chamber or compartment near the chest wall of a patient can be filled to a higher pressure, or can have a greater internal volume, in order to compress the thickest part of the breast first and keep it from sliding from under the compression paddle as the compression force is raised. Alternatively, another construction of the device can be used to a similar end, for example, making the device tilted so it is thicker near the chest wall.

Another device that can be used to improve patient comfort in breast compression is a similar pillow or bag but filled at least partly with a liquid such as water rather that filled only with a gas such as air. In addition to the benefits of a gas-filled device discussed above, the device that is filled at least partly with a liquid such as water would provide some equalization of the x-ray path length that forms the breast image.

Another device for improving patient comfort in breast compression is a sheet of transparent and sufficiently strong material such as Mylar to take over some or all of the functions of a compression paddle. The material may be supported by rods or other holders that flank the breast and are supported and are movable in a manner similar to that of a compression paddle. Alternatively, the material may be supported between rods or other holders that are secured to the breast platform or another part of the mammography system, in which case the need for a compression paddle may be eliminated altogether. The material may be stretchable or otherwise deformable in ways that are not uniform across the portion thereof used to compress the breast. For example, one or more portions, or all the material, closer to the chest wall may stretch or deform less that portions or all the material further from the chest wall of the patient, to thereby compress the thicker part of the breast more. In addition, at least some portions of the material facing the breast may be made sticky, for example by making the material itself sticky or by coating it with a sticky substance, in order to eliminate or reduce slippage between the breast and the material.

Yet another device that improves comfort in breast compression is made wholly or in part of a compressible foam or similar material. The device may have substantially constant thickness in the direction of x-ray flux, or it may be shaped to provide a shallow depression that cradles the breast.

All of the devices listed above can be further improved by being provided with one or more marking portions that are more opaque to x-rays than the rest of the device and thereby affect the x-ray image in a beneficial way. The image artifact caused by a marking portion can be used for any one of a number of purposes. For example, it can serve as an indicator in the image that a device has been used to improve comfort during compression. It can further indicate the type of device that was used, its position and/or orientation relative to the breast or to another structure, and/or as another aid in imaging or interpreting the image. This deliberate image artifact can have characteristics that make it an acceptable addition to the image, even if it is within the outline of the imaged breast. For example, it can be at a place in the image that does not affect diagnostic or screening use or some other use of the image, it can be removed by computer-processing the image (since the characteristics of the artifact are known), or the artifact may inherently be absent from processed images based on the raw x-ray data (for example, the artifact may be positioned such that it is not seen in reconstructed tomosynthesis slice images that are of medical or other interest. For example, the artifact may show up in an image as a straight line shadow that can be safely ignored in assessing the image, or as a shadow in some other shape that can be ignored. The artifact may appear as a shadow of a shape that contains useful information, such as a circle, a rectangle or a trapezoid, for example, that evidences positional, orientation, or some other information about the device, the breast, or the imaging procedure. The artifact-causing substance can be a part of the same substance of which the rest of the device is made but is made thicker or denser at desired location. Alternatively, a different substance can be used, such as a strip or some other shape of aluminum or another substance that is more x-ray opaque than the rest of the device and is incorporated in or attached to the device. As a non-limiting example, an adhesive-backed strip of aluminum can be attached to the device, at a desired place on the device, before compression or even at some stage of the compression or after compression and before taking an x-ray image.

BRIEF DESCRIPTION OF THE DRAWINGS

FIG. 5 is a sectional view along a plane parallel to a patient's chest wall and illustrates a sheet-like breast compression device utilizing material stretched between two rods.

FIG. 6 is a plan view of the arrangement seen in FIG. 5 showing a compression system utilizing material stretched between two rods. The breast is underneath the membrane, and is visible because the membrane is transparent.

FIG. 7 is a perspective view of another sheet-like breast compression device. Compression system showing rod that mylar will be stretched across, and the mounting mechanism allowing mounting to the gantry.

FIG. 8 is a perspective view illustrating prior art and current methods of mounting of a compression paddle to gantry.

FIG. 9 is a sectional view similar to FIG. 5 but illustrating another way of supporting a sheet-like compression device, a compression system utilizing material stretched between two rods or rollers fastened to lower breast platform or Bucky.

FIG. 10 is a sectional view similar to FIGS. 5 and 9 but illustrating another type of a breast compression device, a compression system employing a deformable compression paddle.

FIGS. 11-15 illustrate known breast compression of breast support devices.

FIG. 11 Prior Art.: Tilting FAST paddle by Lorad

FIG. 12 Prior Art: Tilting FAST paddle by Lorad showing a breast in compression

FIGS. 13-14 Prior Art: compression pads. From Biolucent website www.biolucent.com/info.html FIG. 15 Prior Art. Shows compression method for biopsies. From Scientific Biopsy website: www.sbiopsy.com/Breast-Compression.html.

FIG. 16 illustrates a known compression paddle with an opening for a biopsy or needle localization.

FIG. 17 illustrates in plain view two examples of shapes of compression devices to accommodate cutout in paddle, especially suitable for use in needle biopsy.

DETAILED DESCRIPTION OF PREFERRED EMBODIMENTS

Figure 1:
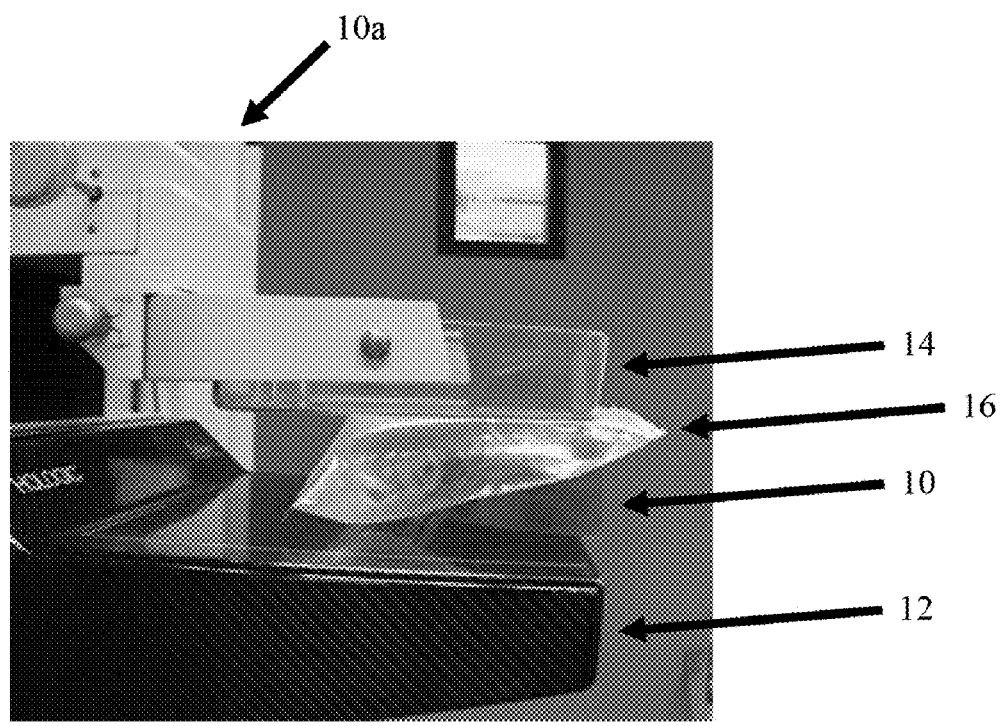
FIG. 1 illustrates a side view of a breast phantom positioned for x-ray imaging between a breast platform and a compression paddle, with a device in the form of a gas-filled bag or pillow between the compression paddle and the breast.
Figure 2:
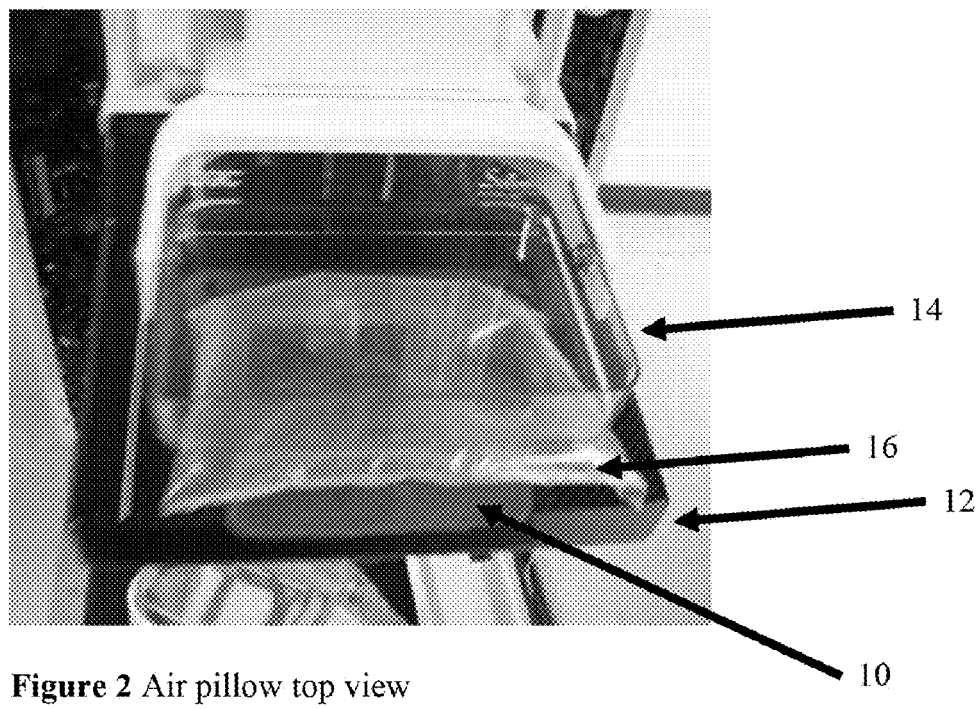
FIG. 2 is a perspective view of the arrangement shown in FIG. 1.
Figure 3:
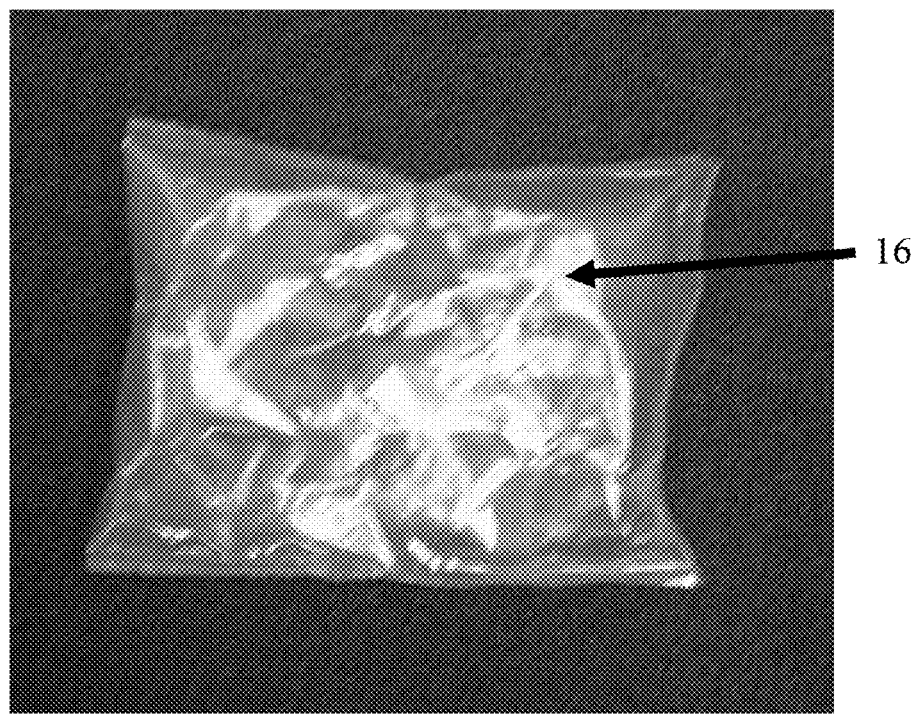
FIG. 3 is a perspective view of the device shown between the breast and the compression paddle in FIGS. 1 and 2.

FIG. 1 illustrates a breast phantom 10 positioned for x-ray examination in a mammography or tomosyntesis system generally indicated at 10a. One example of a system 10a is the digital mammography system offered for sale currently by the Lorad division of Hologic, Inc. under the designation Selenia. Phantom 10 is between a breast platform 12 and a compression paddle 14. A device 16, in the form of a gas-filled bag or pillow, is placed between the breast and the compression paddle. In actual use, the patient would be sitting or standing to the right of breast platform 12 for an x-ray image taken at the CC orientation, with a breast 10 in place of phantom 10. The patient's chest wall would be generally along the vertical. FIG. 2 illustrates in perspective view the same arrangement, and FIG. 3 illustrates the device as it is before being compressed between the breast and the compression paddle. A similar device can be compressed between breast 10 and breast platform 12 in addition or instead of placing a device between breast 10 and compression paddle 14. Breast platform 12 typically has a flat surface on which the breast rests, and is above the image plane at which the x-ray image is formed. There may or may not be a Bucky grid device between breast platform 12 and the image plane. Typically, the image plane in digital mammography and in tomosynthesis systems is at a flat panel digital imager that may use direct conversion of x-ray energy into electrical signals or may use indirect conversion such as by converting x-ray energy to light energy and light energy to electrical signals. In each case, the surface on which the breast rests typically is flat.

Figure 4:
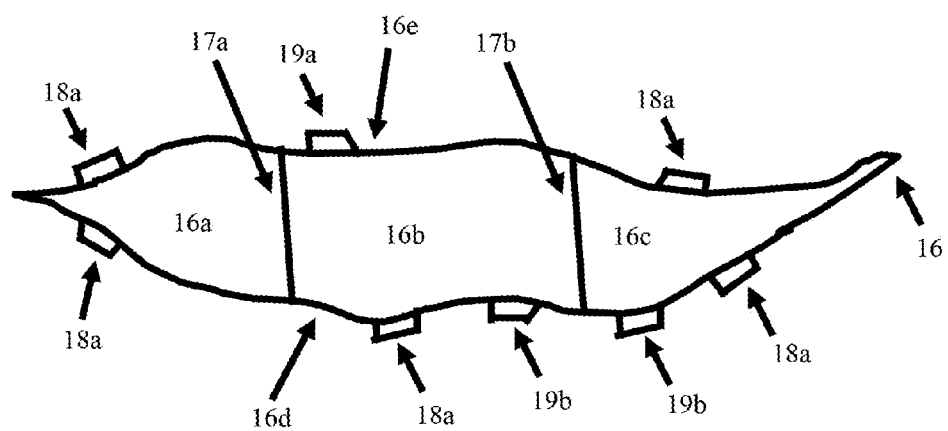
FIG. 4 illustrates a sectional view through the device of FIG. 3, modified by showing or illustrating compartments, elements to increase friction, and markers that are more opaque to x-ray flux.

FIG. 4 illustrates a section through the device of FIGS. 1-3, along a vertical plane parallel to the chest wall of a patient when device 16 is in use for x-ray imaging of the breast in the CC orientation. Device 16 can be a pillow or bag of a transparent plastic sheet material that allows visualization of the breast during compression. It can be made using standard manufacturing methods used for cushioning products during shipping, and can be manufactured inexpensively. Device 16 can have a single chamber filled with a gas such as air, or it can comprise two or more chambers or compartments that can be the same or different in volume and can be filled with gas at the same or different pressure. For example, the gas pressure in device 16 can be close to atmospheric pressure, but the amount of gas is such that the device is loosely filled and its walls are not stretched and are somewhat loose and perhaps wrinkled. In the example of FIG. 4, device 16 comprises three chambers 16a, 16b and 16c, separated by partition walls 17a and 17b. The number or chambers can be as few as two, or as high as desired. Partition walls such as 17a and 17b can be parallel to each other, or at an angle to each other, or can intersect each other such that the number of chambers is two or more in each of two or even three orthogonal directions. At least a part of the bottom wall 16d and/or the top wall 16e can be made of a material that is sticky with respect to patient skin and/or the material of breast platform 12 and compression paddle 14 coming in contact with device 16 in order to prevent or at least reduce slippage and movement between breast 10 and device 16 and/or between device 16 and breast 10 and breast platform 12 and/or compression paddle 14 as the breast is compressed and while an x-ray image is taken. In the alternative or in addition, at least portions of the bottom side 16d and/or top side 16e can be provided with layers 18a of a material that is sticky at least at its side facing out, such as pressure activated adhesive tape. Two-sided adhesive tape can be used for that purpose, and can be applied either when needed or can be pre-applied at an earlier time and protected by easy-release covers until ready to use. One or more markers such as 19a and 19b can be incorporated in or added to device 16 in order to affect one or more x-ray images taken with device 16 in place. Any one or more of the markers can be made using the same material as the rest of device 16 but making it thicker or denser, or by using a different material that is incorporated in or secured (e.g., adhered) to device 16.

In order to achieve desired degrees of breast compression, portions of device 16 can be made to deform differently under pressure. For example, one or more portions close to the chest wall of a patient can be made stiffer or less deformable to thereby pull or push into the field of view of the x-ray image more of the tissue close to the chest wall. This can be accomplished by making the gas pressure higher or the gas volume greater at one or more of the chambers close to the chest wall of the patient, or in some other way, such as by making the material of the walls of such chambers stiffer or thicker. A number of devices such as 16 can be pre-filled with gas and stored for use, or they can be stored with little or no gas inside to take up less volume, and filled with the desired amount of gas, for example through a valve (not shown) when the need arises. Device 16 can be a single use device, or a multiple use device. When in multiple use, device 16 can be secured temporarily to breast platform 12 and/or compression paddle 14 using a suitable adhesive or adhesive strip or by mechanical means such as hook-and-loop strips (not shown), so it can be used for a succession of x-ray images for the same patient or successive patients.

As an alternative, device 16 may be filled partly with a liquid such as water and partly with a gas such as air, or it may be filled only with liquid. If device 16 has two or more chambers, the different chambers may have different contents in terms of ratio or liquid to air, and one or more may contain solely or mostly liquid while one or more other chambers contain solely or mostly gas.

FIGS. 5-11 illustrate another example of an improved device 50 for compressing breast 10. Device 50 comprises a sheet of material that is transparent to visible light and is essentially transparent to the x-ray flux used in mammography or tomosynthesis. One example of such material is a thin sheet of a material known by the trade name Mylar. Another is a sheet of rubber or rubber-like material. The material needs to be only sufficiently strong to compress the breast to the desired degree of compression. As illustrated in FIGS. 5 and 6, the sheet material that forms device 50 can be fed out of a roll 52a wound on a suitable rod or similar support and taken up on a roll 52b wound on a similar rod or other support. The supports for rolls 52a and 52b can be arranged in any manner that permits pay-out and take-in of a desired length of sheet material and also control the tension of the sheet material and thus the force that it exerts on breast 10. For example, the supports for rolls 52a and 52b can be friction-mounted for rotation about their respective axes, or can be clutched, or otherwise constrained against free rotation, and can be rotated only as desired manually or with suitable electric or other motors. As illustrated in FIG. 7, the sheet material can be stretched between rods attached to a conventional compression paddle holder that can be mounted to system 10a as illustrated in FIG. 8. Alternatively, the sheet material forming compression device 50 can be stretched between support elements such as rollers or other tension devices that are secured to breast platform 12 as illustrated in FIG. 9.

In use, the sheet material forming compression device 50 is lowered toward the breast, for example using the same mechanism that lowers the compression paddle in a system such as 10a and is tightened as desired to achieve the desired level of breast compression. In the example of FIG. 9, the sheet material is loosened to position breast 10 under it and is then tightened as needed.

The sheet material forming compression device 50 can have different mechanical characteristics at different areas thereof that contact breast 10. For example, the material can be made such that it exerts greater force where the breast is thicker. This can be achieved in any number of ways, for example by making the material thicker at the portion that would be closer to the patient's chest wall in use, or by varying the composition of the material in a direction away from the patient's chest wall, or in some other way. As in the case of device 16, at least a portion of at least one side of the material forming device 50 can be made sticky or its coefficient of friction with breast 10 can be increased to prevent or reduce slippage between device 50 and breast 10 and to pull and keep more tissue into the x-ray image field. Also as in the case of device 16, the degree of x-ray opaqueness of the material forming device 50 can be selectively controlled, or x-ray opaque material can be incorporated in or added to device 50 for the reasons and in the manner discussed in connection with device 16. A new length of material can be used for device 50 for each new patient, or for each breast of the same patient, or for each imaging position of a breast, or even for each new x-ray exposure.

FIG. 10 illustrates yet another example of a device to improve breast compression, this time in the form of a device 100 made of a compressible material such as foam that is secured to the underside of a conventional compression paddle, for example with an adhesive or mechanically. Device 100 can have uniform thickness in the direction of x-ray flux before compressing the breast and deforming as illustrated in FIG. 10 such that its underside become concave. In the alternative, device 100 can be formed with varying thickness. For example, its underside can be somewhat concave and become more so as breast 10 is compressed, and/or its thickness can increase toward the patient's chest wall so as to exert greater force at the thickest part of the breast close to the chest wall. The stiffness of the material forming device 100 can further vary in a direction along the patient's chest wall. For example, the material can be made softer, and can even be in the form of a gas or liquid filled chamber, around the central axis of breast 10, and can be made stiffer closer to the laterals sides (the left and right edges in FIG. 10), thereby increasing patient comfort and also stability of device 100. The material for device 100 can be substantially transparent to the x-ray flux used in mammography or tomosynthesis, or it can be made sufficiently opaque to that x-ray flux to affect the x-ray image. For example, the material can be made sufficiently opaque to that flux to provide some degree of equalization of the x-ray path length over the entire breast. As in the case of devices 16 and 50, the underside of device 100 can be made sticky to resist slippage relative to breast 10 and chest wall skin as the breast is compressed, and device 100 can incorporate material serving as markers that are more opaque to the x-ray flux and therefore affect the resulting x-ray image of breast 10.

The Soft Compression Device (Patent Pending), shown in FIG. 15, is a recently developed optional new unit for providing maximum comfort. The Soft Compression Device (SCD) uses an elastic band that wraps around a significant part of the breast and imposes a high immobilization force on the breast but with less compression and less discomfort than the flat plate unit. The SCD is disposable for achieving an ultimately clean procedure. The SCD comprising a soft compression base 151 and a flexible band 152 that wraps around a significant part of the breast imposing high holding force with less discomfort and pains.

FIG. 16 illustrates an example of a paddle for needle localization or biopsy. The paddle may have one or more central cutouts 160. The periphery of the cutout 161 may have ruler markings on it to guide a needle to a specific x, y location. The paddle may be used to guide needles for localization or biopsy to a specific location in the breast. Pillows or liquid-filled bag solutions as described above may be adapted to this form of paddle.

FIG. 17 shows two version of an improved compression device adapted for use in needle biopsy. One device 170a uses a donut shape, with a hole in the center allowing the biopsy needle access. The donut shape shown here is rectangular, although other shapes having a central access area or an access area offset from the device center may be used. Another compression device 170b is U-shaped. This also has central access area, but the pillow or bag does not go all the way around the central hole. The hole may alternatively be off-center. Tie open area of this pillow 170b at its bottom could be oriented towards the chest wall, or in some other orientation. Except for the fact that devices 170a and 170b have opening for biopsy needle access, they can have any or all of the other attributes and characteristics of compression devices 16, 50 and 100 discussed above, including chambers that differ from each other in size or content and markers that are more opaque to the x-ray flux used in mammography or tomosynthesis. In a cross-section in a vertical plane, compression devices 170a and 170b would be similar to devices 16, 50 and 100, except for the hole for a biopsy needle, and may be filled with gas such as air or liquid such as water, or may be made of a compressible material such as foam.

The invention claimed is:

1. An X-ray breast imaging method comprising:
   compressing a patient's breast against a container having fluid therein and being non-flat before compression;
   said compressing redistributing at least some of the fluid in said container and deforming the container;
   taking one or more x-ray imaging exposures using x-rays that traverse the compressed breast and the deformed container before reaching an imaging plane.

2. The X-ray breast imaging method as in claim 1 in which said compressing comprises compressing the patient's breast against a container that is substantially transparent to visible light.

3. The X-ray breast imaging method as in claim 1 in which said compressing comprises compressing the patient's breast against a container having markings that are imaged by x-rays in said one or more imaging exposures.

4. The X-ray breast imaging method as in claim 1 in which said compressing comprises contacting a chest wall of the patient adjacent the breast with a portion of said container that is provided with friction-enhancing properties and thereby helping draw patient tissue away from the patient's chest wall and toward said image field.

5. The X-ray breast imaging method as in claim 4 in which said compressing comprises providing said friction-enhancing properties by providing at least a portion of said container with a sticky surface.

6. The X-ray breast imaging method as in claim 1 in which compressing comprises compressing the patient's breast against a container in which said fluid is gas.

7. The X-ray breast imaging method as in claim 1 in which said fluid comprises compressing the patient's breast against a container in which said fluid is a liquid.

8. The X-ray breast imaging method as in claim 1 in which said compressing comprises compressing the patient's breast against a container that has at least two compartments for said fluid.

9. The X-ray breast imaging method as in claim 8 in which said compressing deforms said compartments differently.

10. The X-ray breast imaging method as in claim 1 in which said taking of x-ray imaging exposures comprises taking mammogram images.

11. The X-ray breast imaging method as in claim 1 in which said taking of x-ray imaging exposures comprises taking tomosynthesis images.

12. The X-ray breast imaging method as in claim 1 in which said taking of x-ray exposures comprises causing the imaging x-rays to traverse the container before traversing the patient's breast.

13. An x-ray breast imaging system comprising:
    a container having a fluid contained therein and being non-flat before compression;
    a breast compressing structure selectively compressing a patient's breast against the container;
    said compressing redistributing at least some of the fluid in said container and deforming the container;
    a gantry on which the breast compressing structure is mounted;
    an x-ray source emitting imaging x-rays and an x-ray receptor receiving said x-rays after passage thereof through the patient's breast and said container to form an image of the patient's breast.

14. An x-ray breast imaging system as in claim 13 in which said container is sufficiently transparent to visible light to facilitate viewing the breast through the container.

15. An x-ray breast imaging system as in claim 13 in which said container comprises markings that are sufficiently opaque to x-rays to be imaged in said x-ray imaging.

16. An X-ray breast imaging method comprising:
    providing a generally flat breast platform, sheet material supports that are out of contact with a patient's breast, and sheet material extending between said supports and over the breast;
    compressing the breast between said sheet material and the breast platform while maintaining said supports out of contact with the breast;
    imaging the compressed breast with x-rays traversing the sheet material and the breast before impinging on an x-ray imaging receptor;
    wherein said sheet material is sufficiently transparent to visible light to permit visualization of the breast through the sheet material; and
    wherein said sheet requires greater force to stretch at portions thereof that contact the patient's breast closest to the patient's chest wall than at portions contacting the breast closer to the nipple.

17. An X-ray breast imaging method comprising:
    providing a generally flat breast platform, sheet material supports that are out of contact with a patient's breast, and sheet material extending between said supports and over the breast;
    compressing the breast between said sheet material and the breast platform while maintaining said supports out of contact with the breast; and
    imagine the compressed breast with x-rays traversing the sheet material and the breast before impinging on an x-ray imaging receptor;

wherein said sheet material is sufficiently transparent to visible light to permit visualization of the breast through the sheet material; and including a feed roll and a take-up roll flanking the breast, said feed roll having wound thereon a supply of said sheet material and said take-up roll taking up a portion of said sheet material that has previously been used for compressing a breast.

* * * * *